(12) United States Patent
Yetkinler et al.

(10) Patent No.: US 7,252,672 B2
(45) Date of Patent: *Aug. 7, 2007

(54) USE OF VIBRATION WITH ORTHOPEDIC CEMENTS

(75) Inventors: Duran Yetkinler, Cupertino, CA (US); David Delaney, Scotts Valley, CA (US); Brent R. Constantz, Menlo Park, CA (US)

(73) Assignee: Skeletal Kinetics, LLC, Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/797,907

(22) Filed: Mar. 9, 2004

(65) Prior Publication Data

US 2005/0059979 A1 Mar. 17, 2005

Related U.S. Application Data

(63) Continuation-in-part of application No. 10/661,356, filed on Sep. 11, 2003.

(51) Int. Cl.
*A61B 17/58* (2006.01)
*A61F 2/00* (2006.01)

(52) U.S. Cl. ........................................ 606/92

(58) Field of Classification Search .......... 606/86, 606/92, 93, 94, 95, 169, 170, 171; 623/23.61, 623/23.62; 433/86; 601/2–4; 604/22, 187, 604/82–92; 366/110, 112, 114; 222/161, 222/196

See application file for complete search history.

(56) References Cited

U.S. PATENT DOCUMENTS

| | | | |
|---|---|---|---|
| 4,160,012 A | 7/1979 | Ono et al. | |
| 4,161,511 A | 7/1979 | Shiraki et al. | |
| 4,429,691 A | 2/1984 | Niwa et al. | |
| 4,463,875 A * | 8/1984 | Tepic | 222/82 |
| 4,497,075 A | 2/1985 | Niwa et al. | |
| 4,653,957 A | 3/1987 | Smith et al. | |
| 4,787,751 A * | 11/1988 | Bakels | 366/110 |
| 4,990,163 A | 2/1991 | Ducheyne et al. | |
| 5,045,054 A * | 9/1991 | Hood et al. | 604/22 |
| 5,222,937 A * | 6/1993 | Kagawa | 604/22 |
| 5,281,265 A | 1/1994 | Liu | |
| 5,304,577 A * | 4/1994 | Nagata et al. | 524/417 |
| 5,318,570 A * | 6/1994 | Hood et al. | 606/99 |
| 5,489,308 A * | 2/1996 | Kuslich et al. | 623/17.11 |
| 5,496,399 A * | 3/1996 | Ison et al. | 106/35 |

(Continued)

FOREIGN PATENT DOCUMENTS

DE 100 57 616 A1 5/2002

(Continued)

*Primary Examiner*—Anu Ramana
(74) *Attorney, Agent, or Firm*—Bret E. Field; Bozicevic, Field & Francis LLP

(57) ABSTRACT

Methods of employing bone defect filling, e.g., orthopedic cements, such as calcium phosphate cements and the like, are provided. A feature of the subject methods is that vibration is employed in conjunction with the use of the cement, e.g., in preparation of the cement, in preparation of the target site, in delivery of the cement to the target site, and/or following delivery of the cement to the target site. Also provided are devices, systems and kits that find use in practicing the subject methods. The subject methods, devices and systems find use in a variety of different applications.

11 Claims, 5 Drawing Sheets

U.S. PATENT DOCUMENTS

| | | | |
|---|---|---|---|
| 5,525,148 A | | 6/1996 | Chow et al. |
| 5,545,254 A | | 8/1996 | Chow et al. |
| 5,580,623 A | | 12/1996 | Fulmer et al. |
| 5,639,238 A | * | 6/1997 | Fishburne, Jr. ............. 433/215 |
| 5,647,851 A | * | 7/1997 | Pokras ...................... 604/131 |
| 5,679,294 A | | 10/1997 | Umezu et al. |
| 5,695,729 A | | 12/1997 | Chow et al. |
| 5,697,981 A | | 12/1997 | Ison et al. |
| 5,900,254 A | | 5/1999 | Constantz |
| 5,954,867 A | | 9/1999 | Chow et al. |
| 5,962,028 A | | 10/1999 | Constantz |
| 5,968,253 A | | 10/1999 | Poser et al. |
| 5,976,105 A | * | 11/1999 | Marcove et al. ............ 604/500 |
| 5,976,234 A | | 11/1999 | Chow et al. |
| 5,997,624 A | | 12/1999 | Chow et al. |
| 6,005,162 A | | 12/1999 | Constantz |
| 6,027,742 A | | 2/2000 | Lee et al. |
| 6,083,229 A | * | 7/2000 | Constantz et al. ............ 606/92 |
| 6,139,320 A | * | 10/2000 | Hahn ........................ 433/119 |
| 6,139,578 A | | 10/2000 | Lee et al. |
| 6,149,655 A | * | 11/2000 | Constantz et al. ............ 606/94 |
| 6,214,012 B1 | * | 4/2001 | Karpman et al. ............. 606/93 |
| 6,224,635 B1 | * | 5/2001 | Ricci et al. ............. 623/23.62 |
| 6,241,734 B1 | * | 6/2001 | Scribner et al. ............. 606/93 |
| 6,340,299 B1 | * | 1/2002 | Saito ........................ 433/80 |
| 6,375,935 B1 | | 4/2002 | Constantz |
| 6,494,611 B2 | | 12/2002 | Edwards et al. |
| 6,593,394 B1 | * | 7/2003 | Li et al. ..................... 523/113 |
| 6,602,229 B2 | * | 8/2003 | Coss ......................... 604/187 |
| 6,610,079 B1 | * | 8/2003 | Li et al. ..................... 606/232 |
| 6,620,162 B2 | * | 9/2003 | Kuslich et al. ............... 606/53 |
| 6,733,451 B2 | * | 5/2004 | Rabiner et al. ............. 600/439 |
| 6,808,561 B2 | * | 10/2004 | Genge et al. .............. 106/690 |
| 6,832,988 B2 | * | 12/2004 | Sproul ...................... 600/459 |
| 6,872,403 B2 | * | 3/2005 | Pienkowski et al. ........ 424/422 |
| 2002/0158167 A1 | | 10/2002 | Lee et al. |
| 2002/0183851 A1 | * | 12/2002 | Spiegelberg et al. ..... 623/22.12 |
| 2003/0199615 A1 | | 10/2003 | Chaput et al. |
| 2004/0024410 A1 | * | 2/2004 | Olson et al. ................. 606/93 |
| 2004/0078685 A1 | | 4/2004 | Tee |

FOREIGN PATENT DOCUMENTS

| | | |
|---|---|---|
| EP | 0 353 241 | 3/1988 |
| EP | 0 501 595 | 3/1994 |
| JP | 04127668 | 5/1992 |
| WO | WO 90/04953 | 5/1990 |

* cited by examiner

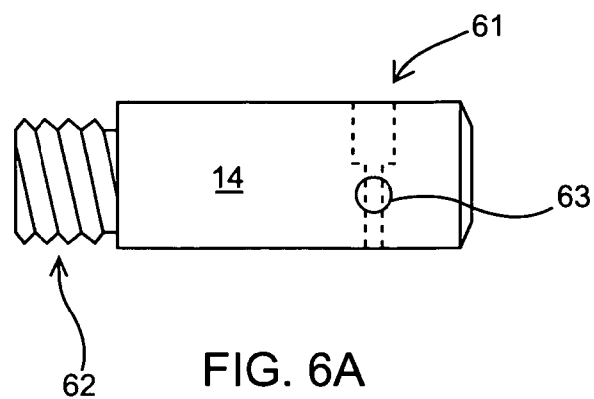
FIG. 6A
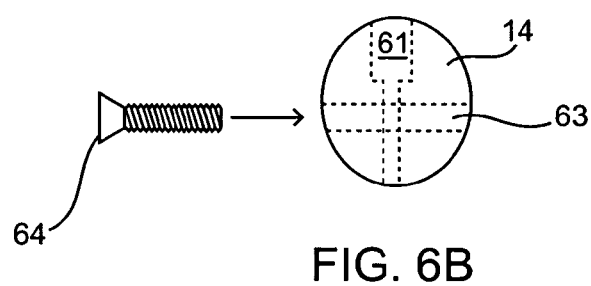
FIG. 6B
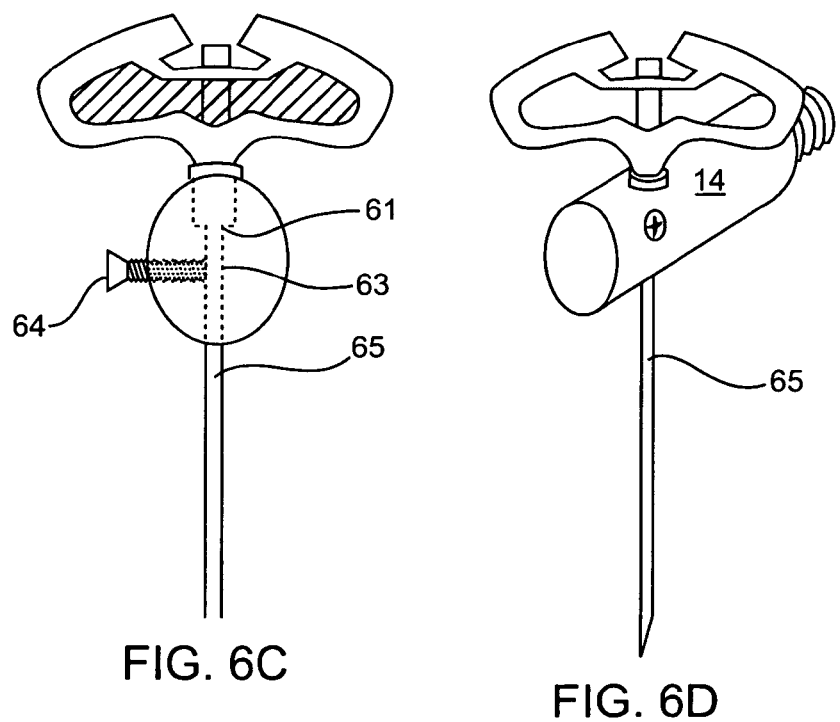
FIG. 6C
FIG. 6D

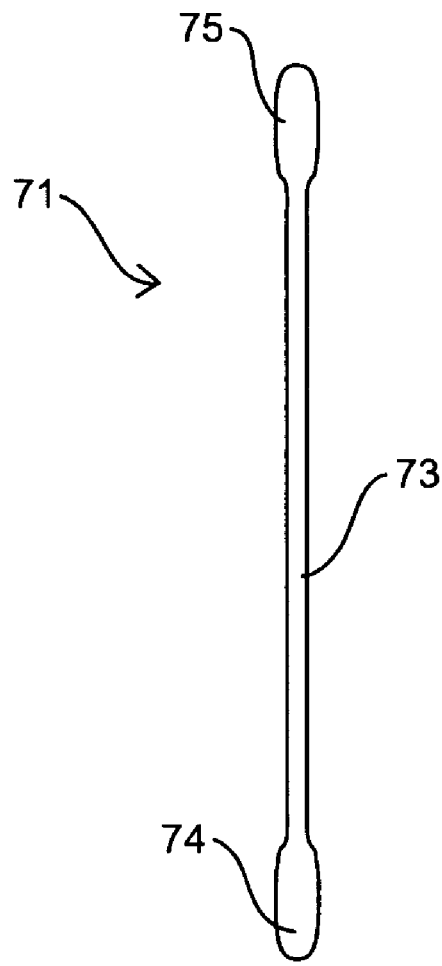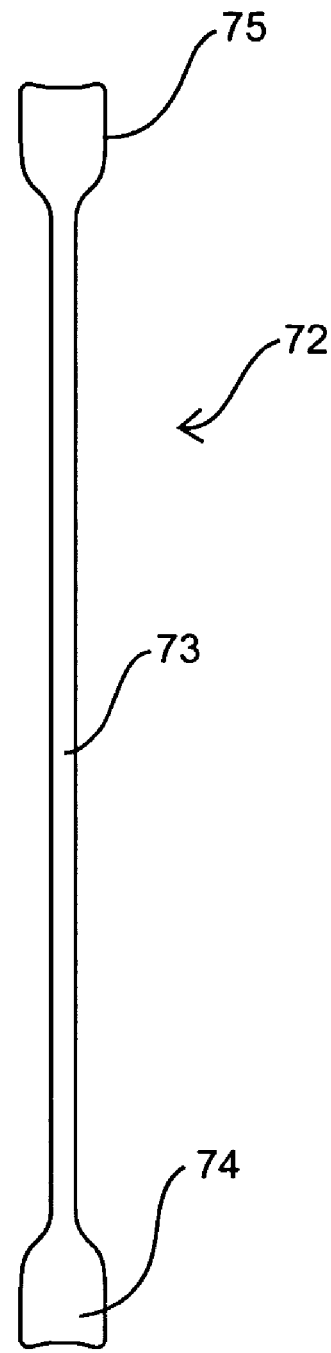
FIG. 7A
FIG. 7B

USE OF VIBRATION WITH ORTHOPEDIC CEMENTS

CROSS-REFERENCE TO RELATED APPLICATIONS

This application is a continuation-in-part of application Ser. No. 10/661,356 filed Sep. 11, 2003; the disclosure of which is herein incorporated by reference.

INTRODUCTION

1. Field of the Invention

The field of this invention is delivery of orthopedic cements.

2. Background

Orthopedic/bone defect filling cements find use in a variety of different applications, including orthopedic and dental applications. A variety of different orthopedic cements have been developed to date, where such cements include both polymeric based cements, such as PMMA, as well as mineral based cements, e.g., calcium and/or phosphate containing cements. As the field matures, ever more chemical formulations and applications are being developed in which orthopedic cements find use.

While the field of orthopedic/bone defect filling cements as progressed greatly, there continues to be a need for improvements in this area. For example, as calcium phosphate cements have been refined, delivery protocols and devices for use in the same have also been developed. Where the target bone site is a porous cancellous structure, e.g., as may be encountered in a reduced fracture or inside a compromised vertebral body, one approach is to deliver the cement under high pressure, so that it adequately penetrates the cancellous bone tissue. However, a disadvantage of high-pressure delivery methods is that they can result in penetration beyond the site of interest, and delivery may be hard to control, such that even when the pressure source is removed, cement still penetrates the tissue, perhaps to undesirable areas and/or causing undesirable side effects. Specifically, pressurization of cement in the body often causes emboli of cement or fat which can result in death of the patient or other adverse events.

An alternative to delivery under pressure is to remove the cancellous tissue from the target site to produce a true void space into which the cement composition may be introduced. In certain embodiments, a void space may be produced by introducing a balloon into the target site and expanding the balloon in a manner that compresses the cancellous tissue and results in the production of a void space at the target site. However, there are disadvantages to this approach as well, such as the loss of cancellous tissue. Furthermore, the expansion of the balloon can cause fat emboli that can result in patient death or adverse events.

As such, there continues to be an interest in the development of new protocols and devices for use in applications where such cements are employed.

Relevant Literature

U.S. Pat. Nos. of interest include: 6,375,935; 6,139,578; 6,027,742; 6,005,162; 5,997,624; 5,976,234; 5,968,253; 5,962,028; 5,954,867; 5,900,254; 5,697,981; 5,695,729; 5,679,294; 5,580,623; 5,545,254; 5,525,148; 5,281,265; 4,990,163; 4,497,075; 4,429,691; 4,161,511 and 4,160,012. Also of interest is published United States Application No. 2004/0024410 A1.

SUMMARY OF THE INVENTION

Methods of employing orthopedic/bone defect filing cements are provided. A feature of the subject methods is that vibration is employed in conjunction with the use of the orthopedic cement, e.g., in preparation of the cement, in preparation of the target site for the cement, in delivery of the cement to the target site, and/or following delivery of the cement to the target site. Also provided are devices, systems and kits that find use in practicing the subject methods. The subject methods, devices and systems find use in a variety of different applications.

BRIEF DESCRIPTION OF THE FIGURES

FIGS. 1 to 6D provide various views of a pneumatically driven needle vibrating device that may be employed in certain embodiments of the subject invention, e.g., where vibration is employed in conjunction with delivery of a cement to a target bone site.

FIGS. 7A and 7B provide representations of "elevator" devices that may be employed during certain embodiments of the subject invention.

DESCRIPTION OF THE SPECIFIC EMBODIMENTS

Figure 1:
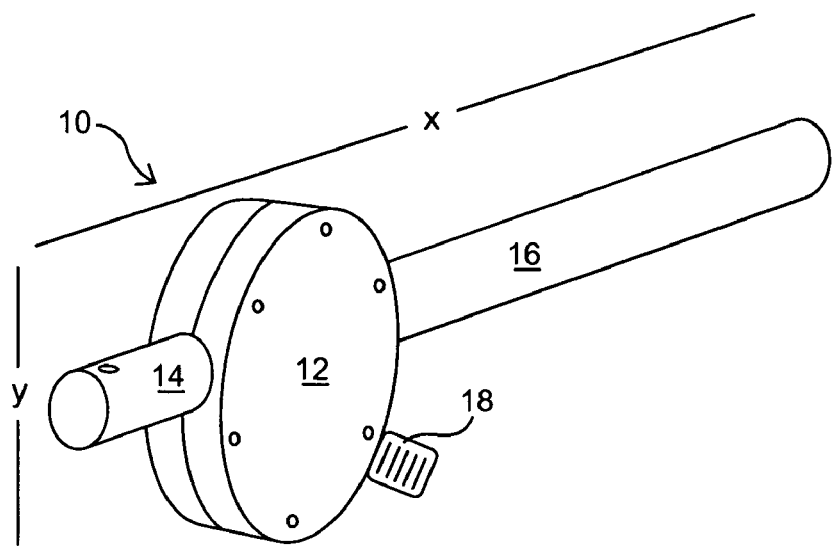

Methods of employing bone defect filling cements, e.g., calcium phosphate cements and the like, are provided. A feature of the subject methods is that vibration is employed in conjunction with the use of the cement, e.g., in preparation of the cement (including combination of the cement components and/or additives to the cement), in preparation of the target site for the cement, in delivery of the cement to the target site, following delivery of the cement to the target site for better penetration, and/or for post delivery modification of the positioned cement, e.g. to modulate the rate of setting of the cement,. Also provided are devices, systems and kits that find use in practicing the subject methods. The subject methods, devices and systems find use in a variety of different applications.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that, as used in this specification and the appended claims, the singular forms "a," "an" and "the" include plural reference unless the context clearly dictates otherwise. Unless defined otherwise all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

Where a range of values is provided, it is understood that each intervening value, to the tenth of the unit of the lower limit, unless the context clearly dictates otherwise, between the upper and lower limit of that range and any other stated or intervening value in that stated range, is encompassed within the invention. The upper and lower limits of these smaller ranges may independently be included in the smaller ranges, and such embodiments are also encompassed within the invention, subject to any specifically excluded limit in the stated range. Where the stated range includes one or both of the limits, ranges excluding either or both of those included limits are also included in the invention.

All publications mentioned herein are incorporated herein by reference for the purpose of describing and disclosing components that are described in the publications that might be used in connection with the presently described invention.

In further describing the subject invention, the subject methods will be described first, as well as representative utilities thereof, followed by a review of representative devices, systems and kits that may be used therein.

Methods

As summarized above, the subject methods are methods of using a bone defect filling (e.g., orthopedic) cement, e.g., calcium phosphate cement composition or the like. A feature of the subject methods is that the cement employed in the methods is employed in conjunction with vibration. By "in conjunction with vibration" is meant that vibratory force is used at some point during the application or protocol in which the orthopedic cement is being used. Put another way, in a given protocol where a cement is used, the protocol is a method according to the present invention if vibration is used at some point during the protocol, e.g., during preparation and/or delivery of the cement to a target bone site, during preparation of the target bone site, following delivery of the composition to a target bone site, etc.

The term vibration is used to refer to a vibratory or oscillating force that is applied to an object, where the nature of the vibratory force and object to which it is applied may vary depending on the particular embodiment of the subject invention. The force may be applied to a target object, e.g., cement, bone defect site, etc., in a variety of different ways. For example, the force may be applied to the object using a mechanical application element, a sonic application element, etc., as described in greater detail below. Accordingly, representative vibratory forces include sonic forces, mechanical forces, etc.

The vibratory force may be characterized in terms of frequency, such as cycles per second (Hertz or Hz), where in certain embodiments the vibratory force applied to an object during the subject methods may have a frequency that ranges from about 0.1-5.0 to about 100,000 Hz or higher, e.g., from about 5.0 to about 50,000 Hz or higher, such as from about 10 to about 35,000 Hz, including from about 20 to about 20,000 Hz. For example, where the vibratory force applied to an object during the subject methods is a sonic force, the force may be infrasonic or ultrasonic, or in the audible range. The vibratory force may also be characterized in terms of its amplitude or magnitude of vibration. By "amplitude" is meant the movement in any direction. In representative embodiments, the amplitude of the applied vibratory force will range from about 1 Angstrom to about 1 mm, such as from about 1 to about 100 microns, including from about 10 to 50 microns.

Pursuant to the invention, vibration may be employed at one or more points during a given orthopedic cement protocol. Typically, orthopedic cement protocols at least include: cement preparation, target site preparation, cement delivery to a target site; and optionally post delivery cement modification. Representative points at which vibration may be employed include, but are not limited to: cement preparation; target site preparation; cement delivery to a target site; and post delivery modification of the delivered cement.

Each of these different representative times or points at which vibration may be employed is now reviewed separately in greater detail.

In certain embodiments of the subject invention, vibration is used in conjunction with at least the preparation of an orthopedic cement. By used in conjunction with the preparation of an orthopedic cement is meant that vibration is employed at some point during the period in which the cement precursors of the cement, e.g., liquid and solid reagents or cement components, are combined to produce a flowable cement product composition. With many orthopedic cements of interest, dry and liquid precursors, e.g., a powder and setting liquid, are combined to a produce a flowable cement composition product that, over time, sets into a solid material. In certain embodiments of the subject invention, vibration is employed by applying a vibratory force, e.g., sonic or mechanical, to the precursors of the flowable composition, e.g., during mixing of the precursors. For example, in certain representative embodiments, vibration may be applied to the container or vessel in which the flowable cement composition is prepared, and thereby applied to the flowable cement composition as it is being prepared.

In certain of these representative embodiments, the vibratory force that is applied to the cement may have a frequency ranging from about 0.1 Hz to about 100,000 Hz, such as from about 5 Hz to about 50,000 Hz, including from about 100 Hz to about 5000 Hz, and an amplitude ranging from about 1 angstrom to about 5 mm, such as from about 1 micron to about 1 mm, including from about 10 micron to about 500 micron.

The vibratory force may be applied to the cement components for the duration of the preparatory time or for a portion thereof, e.g., while the initial components are combined, while additives are combined with the product of mixing of the initial components, etc. In certain representative embodiments, vibration is applied for a duration ranging from about 1 sec to about 5 minutes, such as from about 10 sec to about 1 minute, including from about 15 sec to about 30 sec.

In certain embodiments, vibration is employed in conjunction with at least preparation of the target bone site. In the subject methods, the target bone site may be any of a variety of different bone sites. In many embodiments, the target bone site is an interior target bone site, e.g., an interior region of a bone, as a cancellous domain bounded by cortical walls. Often, the target bone site is made up of cancellous tissue, into which it is desired to penetrate the orthopedic cement to produce a cancellous bone/cement composite structure. Representative cancellous bone target sites of interest include, but are not limited to, those found in: vertebral bodies, Colles' fractures, proximal humerus fractures, tibial plateau fractures, calcaneous fractures, and the like.

In these embodiments, vibration may be applied to the target bone site using any convenient protocol, depending on the desired outcome of the use vibration in target bone site preparation. For example, in certain embodiments, preparation of the target bone site may include removal of marrow an other materials from the bone site, e.g., the methods may include a marrow or hematoma removal step, where material, e.g., marrow, hematoma, at the target site is removed, e.g., before and/or during delivery of the cement composition, so as to further enhance penetration of the cement into the target site. For example, the marrow may be removed by aspiration from the target bone site. More specifically, marrow may be aspirated from one side of the target site before or as cement is introduced into the other side. In these embodiments, a vibratory force may be applied to the target bone site to enhance the rate and/or efficiency of marrow, e.g., fatty marrow, removal.

In certain of these representative embodiments, the vibratory force that is applied to the target bone site may have a frequency ranging from about 1 Hz to about 100,000 Hz, such as from about 10 Hz to about 10,000 Hz, including from about 100 Hz to about 1000 Hz, and an amplitude ranging from about 1 Angstrom to about 5 mm, such as from about 1 micron to about 100 micron, including from about 5 micron to about 50 micron. In certain representative embodiments, vibration is applied for a duration ranging from about 0.1 sec to about 10 minutes, such as from about 1 sec to about 5 minute, including from about 10 second to about 1 minute.

In certain embodiments, vibration is employed in conjunction with delivery of the cement to a target site. In other words, a vibratory force is applied to the cement composition during delivery to the target site, such as a target bone site. Put another way, the cement composition is vibrated as it is being delivered to the target bone site.

While the cement composition may be vibrated using any convenient protocol, in many embodiments the cement is vibrated by applying vibratory force to a cement delivery element, e.g., needle, which is conveying the cement to the target bone site. The amount of vibratory force that is applied to the cement, e.g., through application to the delivery element, is typically sufficient to provide for highly controlled penetration of the cement through cancellous bone tissue. By "highly controlled penetration" is meant penetration of the cement through cancellous bone tissue in manner that can be stopped at substantially the same time as cessation of vibration, such that when vibration stops, the cement no longer moves further into the cancellous tissue, and any movement of the cement into the cancellous tissues continues for no more than about 5 seconds, such as no more than about 1 to about 3 seconds. Where the vibratory force is applied to the cement by applying it to a delivery element for the cement, the delivery element is, in many embodiments, vibrated in the range of about 1 to 100,000 Hz, such as from about 10 to 10,000 vpm, including from about 100 to about 1,000 Hz, and with a force that moves the delivery element a distance in magnitude in either direction of from about 1 Angstrom to about 5.0 mm, such as from about 1 micron to about 100 micron, such as from 5 micron to 50 micron.

A feature of the subject methods of certain of these embodiments is that the cement is delivered in manner that provides for highly controlled penetration without the use of significant back-pressure on the cement. As such, any pressure applied to the cement during delivery does not exceed about 100 psi, and is between about 1 and 100 psi in certain embodiments. In certain of these embodiments, a negative pressure may be present at the target delivery site, which negative pressure enhances entry of the cement composition to the target site. The negative pressure may be produced using any convenient protocol, e.g., the target site preparation protocol described above. Where a negative pressure is present at the target delivery site, the negative pressure may range from about 1 to about 1000 psi, including from about 10 to about 100 psi.

In certain embodiments, a cement is employed in conjunction with hardware to achieve what is known in the art as composite fixation. In composition fixation, the cement may be employed with one or more types of hardware, e.g., screws, plates, wires, etc. In such embodiments, vibration may be applied to the cement during delivery to achieve a superior composite fixation, e.g., in terms of better interface between the cement and hardware components of the composite fixation structure. In many embodiments, the hardware component(s) is delivered/positioned first, followed by delivery of the cement component, which cement component is delivered in conjunction with vibration according to the subject methods.

In certain embodiments, composite fixation may employ the use of what is known in the art as cannulated screws, i.e., screws with hollow centers which have entry and exit ports through which material can be introduced and removed from the hollow center of the screw. In these embodiments, the screw(s) may be placed or positioned in the subject first, e.g., by delivery over a guidewire, according to methods known in the art. Following placement of the screw, the cement is delivered to the site, e.g., through the screw, in conjunction with vibration, where the vibratory force may be applied to the cement itself, a delivery device thereof, and/or the cannulated screw, etc.

In certain embodiments, vibration may be employed in conjunction with post delivery cement modification, e.g., to modulate (for example enhance or impede) the rate of setting of the cement, as desired for a particular application. By selecting the appropriate type, duration and timing of vibratory force, the rate of setting of the cement can be modulated, e.g., increased or decreased, as desired. For example, in certain embodiments, following application or placement of an amount of a cement composition to a target bone site, it may be desirable to decrease or slow the rate at which the cement sets or hardens. For example, a vibratory force may be applied to the cement composition placed or positioned at the target bone site, e.g., to slow cement setting and provide longer time to shape or model the positioned cement composition. For example, in certain embodiments, the cement composition, following placement, may initially set into a first configuration. A vibratory force may be applied to the cement in this first configuration in order to modify it to a second, more desirable configuration. In this manner, the configuration or shape of the positioned or placed cement composition may be fined tuned or tailored to achieve optimal results in a given application. In yet other embodiments, vibration may be applied to further assist the cement in penetrating into space adjacent to the direct site of introduction, e.g., through the cancellous structure of a vertebral body beyond the exact site of implantation or delivery.

In these embodiments where it is desired to slow or impede the rate of cement setting, e.g., by at least about 2-fold, such as by at least about 5-fold, including by at least about 10-fold, the vibratory force that is applied to the delivered cement composition may have a frequency ranging from about 1 to about 100,000 Hz, such as from about 10 to about 10,000 Hz, including from about 100 Hz to about 1000 Hz, and an amplitude ranging from about 1 Angstrom to about 5 mm, such as from about 1 micron to about 100 micron, including from about 5 micron to about 50 micron. In certain representative embodiments, vibration is applied for a duration ranging from about 0.1 sec to about 10 minutes, such as from about 1 sec to about 5 minutes, including from about 10 sec to about 1 minute.

In yet other embodiments, a vibratory force is applied that enhances or accelerates the rate of setting of the cement, e.g., by at least about 2-fold, such as by at least about 5-fold, including by at least about 10-fold. In certain of these representative embodiments, the vibratory force that is applied to the delivered cement may have a frequency ranging from about 1 to about 100,000 Hz, such as from about 10 Hz to about 10,000 Hz, including from about 100 Hz to about 1000 Hz, and an amplitude ranging from about 1 Angstrom to about 5 mm, such as from about 1 micron to about 100 micron, including from about 5 micron to about 50 micron. In certain representative embodiments, vibration is applied for a duration ranging from about 0.1 sec to about 10 minutes, such as from about 1 sec to about 5 minute, including from about 10 sec to about 1 minute.

A wide variety of bone defect filling cements may be employed according to the subject invention. Representative cements include, but are not limited to: polymeric based cements such as polymethylmethacrylate (PMMA); composite cements (acrylic cements in conjunction with ceramics); and calcium and/or phosphate based cements (i.e., cements that include calcium and/or phosphate ions), e.g., calcium sulfate (sulphate) cements; magnesium amonium phosphate cements, calcium phosphate cements, cements containing radioopaque tracer particle that improve fluoroscopic visualization of the cement, etc. However, in certain embodiments of the subject methods, the orthopedic cement that is employed is one that has a specific gravity at 20° C. that is greater than about 1.0, such as greater than about 1.5, greater than about 2.0, including greater than about 2.5, e.g., greater than about 3.0 etc. In certain embodiments, the cement that is employed is one that does not require or benefit from compaction following delivery. Examples of cements that may require or benefit from compaction (and therefore are not employed in certain embodiments of the subject invention) include polymeric cements, e.g., PMMA, as well as granular type bone void filling products, such as the bone filling media described in United States Published Patent Application 2004/0024410.

In certain embodiments, the cements may include imaging or "tracer" elements, e.g., radioopaque or radioopacifier elements, which provide for enhanced imaging of the cement during delivery, e.g., as visualized by radiographic imaging techniques. Representative radiopaque particles that may find use include radiopaque materials selected from a group consisting of barium sulfate, zirconium dioxide, tantalum, tungsten, platinum, gold, silver, stainless steel and titanium. Representative tracer elements and protocols for imaging the same are described in U.S. Pat. Nos. 6,309,420 and 6,273,916; the disclosures of which are herein incorporated by reference.

In certain embodiments, the cement that is employed is a calcium phosphate cement. A variety of calcium phosphate cements may be delivered to a target site according to the subject invention. Representative cements of interest typically include dry reactants that include a calcium source and a phosphate source that are combined with a setting fluid under conditions sufficient to produce a settable, e.g., flowable or moldable, composition that sets into a calcium-phosphate containing product, sometimes even when immersed in a fluid environment.

The dry reactants may include a calcium source and a phosphate source. The dry reactants are typically particulate compositions, e.g., powders, where the particle size of the components of the particulate compositions typically ranges from about 1 to about 1000 microns, usually from about 1 to about 200 microns and more usually from about 1 to about 40 microns.

As mentioned above, the dry reactants may include a calcium source and a phosphate source. The calcium source and phosphate source may be present as a single compound or present as two or more compounds. As such, a single calcium phosphate present in the dry reactants may be the calcium source and the phosphate source. Alternatively, two or more compounds may be present in the dry reactants, where the compounds may be compounds that include calcium, phosphate or calcium and phosphate. Calcium phosphate sources of interest that may be present in the dry reactants include: MCPM (monocalcium phosphate monohydrate or $Ca(H_2PO_4)_2 \cdot H_2O$); DCPD (dicalcium phosphate dihydrate, brushite or $CaHPO_4 \cdot 2H_2O$); ACP (amorphous calcium phosphate or $Ca_3(PO_4)_2 \cdot H_2O$); DCP (dicalcium phosphate, monetite or $CaHPO_4$); tricalcium phosphate, including both α- and β-$(Ca_3(PO_4)_2$, tetracalcium phosphate $(Ca_4(PO_4)_2O$, etc. Calcium sources of interest include, but are not limited to: calcium carbonate ($CaCO_3$), calcium oxide (CaO), calcium hydroxide ($Ca(OH)_2$) and the like. Phosphate sources of interest include, but are not limited to: Phosphoric acid ($H_3PO_4$), all soluble phosphates; MCPM (monocalcium phosphate monohydrate or $Ca(H_2PO_4)_2 \cdot H_2O$) and sodium analogs thereof, e.g., $NaH_2PO_4$, and the like.

The ratios or relative amounts of each of the disparate calcium and/or phosphate compounds in the dry reactant mixture is one that provides for the desired calcium phosphate product upon combination with the setting fluid and subsequent setting. In many embodiments, the overall ratio (i.e., of all of the disparate calcium and/or phosphate compounds in the dry reactants) of calcium to phosphate in the dry reactants ranges from about 4:1 to 0.5:1, usually from about 2:1 to 1:1 and more usually from about 1.9:1 to 1.25:1.

The second component of the calcium phosphate cement compositions is a setting fluid. The setting fluid can be any of a variety of setting fluids known to those of skill in the art. Setting fluids include a variety of physiologically compatible fluids, including, but not limited to: water (including purified forms thereof), aqueous alkanol solutions, e.g. glycerol, where the alkanol is present in minor amounts, preferably less than about 20 volume percent; pH buffered or non-buffered solutions; solutions of an alkali metal hydroxide, acetate, phosphate or carbonate, particularly sodium, more particularly sodium phosphate or carbonate, e.g., at a concentration in the range of about 0.01 to about 2M, such as from about 0.05 to about 0.5M, and at a pH in the range of about 6 to about 11, such as from about 7 to about 9, including from about 7 to about 7.5; and the like.

Of particular interest in certain embodiments is a silicate setting fluid, i.e., a setting fluid that is a solution of a soluble silicate. By solution of a soluble silicate is meant an aqueous solution in which a silicate compound is dissolved and/or suspended. The silicate compound may be any compound that is physiologically compatible and is soluble in water. By soluble in water is meant a concentration of at least about 1%, usually at least about 2% and more usually at least about 5%, where the concentration of the silicate employed typically ranges from about 0-0.1 to 20%, usually from about 0.01-5 to 15% and more usually from about 5 to 10%. Silicate setting fluids finding use with calcium phosphate cements are further described in U.S. Pat. No. 6,375,935; the disclosure of which is herein incorporated by reference.

A variety of calcium phosphate cement compositions are known to those of skill in the art. Cement compositions known to those of skill in the art and of interest include, but are not limited to, those described in U.S. Pat. Nos. 6,027,742; 6,005,162; 5,997,624; 5,976,234; 5,968,253; 5,962,028; 5,954,867; 5,900,254; 5,697,981; 5,695,729; 5,679,294; 5,580,623; 5,545,254; 5,525,148; 5,281,265; 4,990,163; 4,497,075; and 4,429,691; the disclosures of which are herein incorporated by reference.

Of particular interest in certain embodiments is the cement composition disclosed U.S. Pat. No. 6,375,935; the disclosure of which is herein incorporated by reference. A specific representative formulation of interest is provided in the Experimental Section, below.

In preparing such cements, suitable amounts of the dry reactants and the setting fluid of the cement composition to be delivered to the target site are combined to produce a settable or flowable composition. In other words, the ratio of the dry reactants to setting fluid (i.e. the liquid to solids ratio) is selected to provide for a "settable" or "flowable" composition, where by "settable" or "flowable" composition is meant a composition that goes from a first non-solid (and also non-gaseous) state to a second, solid state after setting. In many embodiments, the liquid to solids ratio is chosen to provide for a flowable composition that has a viscosity ranging from that of milk to that of modeling clay. As such, the liquids to solids ratio employed in the subject methods typically ranges from about 0.2 to 1.0, usually from about 0.3 to 0.6. Of particular interest in many embodiments are methods that produce a paste composition, where the liquid to solids ratio employed in such methods typically ranges form about 0.25 to 0.5, usually from about 0.3 to 0.45.

The dry and liquid components are typically combined under agitation or mixing conditions, such that a homogenous composition is produced from the dry and liquid components. Mixing may be accomplished using any convenient means, including manual mixing as described in U.S. Pat. No. 6,005,162 and automated mixing as described in WO 98/28068, the disclosures of which are herein incorporated by reference. Also of interest is the device disclosed in U.S. Pat. No. 5,980,482, the disclosure of which is herein incorporated by reference.

The temperature of the environment in which combination or mixing of the dry and liquid components takes place is sufficient to provide for a product that has desired setting and strength characteristics, and typically ranges from about 0 to 50° C., usually from about 15 to 30° C. Mixing takes place for a period of time sufficient for the flowable composition to be produced, and generally takes place for a period of time ranging from about 15 to 120 seconds, usually from about 15 to 90 seconds and more usually from about 30 to 60 second.

The resultant settable compositions produced by the above-described methods are compositions that set into a biologically compatible, and often resorbable and/or remodelable, product, where the product is characterized by including calcium phosphate molecules not present in the initial reactants, i.e., that are the product of a chemical reaction among the initial reactants.

The term flowable is meant to include paste-like and even clay like compositions, as well as more liquid compositions. As such, the viscosity time of the subject flowable compositions, defined as time periods under which the mixed composition injects through a standard Luer-lok fitting after mixing, typically ranges up to about 10 minutes, usually up to about 7 minutes, such as up to about 4 minutes. Of particular interest in many embodiments are paste compositions that have an injectable viscosity and inject in a time period ranging up to about 5 minutes, such as about up to about 4 minutes. Pastes that stay paste-like for longer periods may be displaced by bleeding bone once implanted into the body, which create a blood interface between the cement and the bone prior to the cement hardening.

The compositions produced by the subject invention set into calcium phosphate mineral containing products. By "calcium phosphate mineral containing" product is meant a solid product that includes one or more, usually primarily one, calcium phosphate mineral. In many embodiments, the calcium phosphate mineral is one that is generally poorly crystalline, so as to be resorbable and, often, remodelable, over time when implanted into a physiologically site. The calcium to phosphate ratio in the product may vary depending on particular reactants and amounts thereof employed to produce it, but typically ranges from about 2:1 to 1.33:1, usually from about 1.8:1 to 1.5:1 and more usually from about 1:7:1 to 1.6:1. Of particular interest in many embodiments are apatitic products, which apatitic products have a calcium to phosphate ratio ranging from about 2.0:1 to 1.25:1, including both hydroxyapatite and calcium deficient analogs thereof, including carbonate substituted hydroxyapatite (i.e. dahilite), etc. The subject paste-like composition is, in many embodiments, one that is capable of setting into a hydroxyapatitic product, such as a carbonated hydroxyapatite, i.e. dahilite, having a carbonate substitution of from about 2 to about 10%, usually from about 2 to about 8% by weight of the final product.

The period of time required for the compositions to harden or "set" may vary. By set is meant: the Gilmore Needle Test (ASTM C266-89), modified with the cement submerged under 37° C. physiological saline. The set times of the subject cements may range from about 30 seconds to 30 minutes, and will usually range from about 2 to 15 minutes and more usually from about 4 to 12 minutes. In many embodiments, the flowable composition sets in a clinically relevant period of time. By clinically relevant period of time is meant that the paste-like composition sets in less than about 20 minutes, usually less than about 15 minutes and often in less than about 10 minutes, where the composition remains flowable for at least about 1 minute, usually at least about 2 minutes and, in many embodiments, for at least about 5 minutes following combination or mixture of the precursor liquid and dry cement components.

The compressive strength of the product into which the settable/flowable composition sets may vary significantly depending on the particular components employed to produce it. Of particular interest in many embodiments is a product that has a compressive strength sufficient for it to serve as at least a cancellous bone structural material. By cancellous bone structural material is meant a material that can be used as a cancellous bone substitute material as it is capable of withstanding the physiological compressive loads experienced by compressive bone under at least normal physiological conditions. As such, the subject flowable paste-like material is one that sets into a product having a compressive strength of at least about 10, usually at least about 25 and more usually at least about 50 MPa, as measured by the assay described in Morgan, EF et al., 1997, Mechanical Properties of Carbonated Apatite Bone Mineral Substitute: Strength, Fracture and Fatigue Behavior. J. Materials Science: Materials in Medicine. V. 8, pp 559-570, where the compressive strength of the final apatitic product may be as high as 60 MPa or higher. Inclusion of the silicate in the setting liquid allows lower liquid to solids ratios to be employed which results in significantly higher compressive strengths. Compressive strengths can be obtained that range as high as 100 to 200 MPa. In certain embodiments, the resultant product has a tensile strength of at least about 0.5 MPa, such as at least about 1 MPa, including at least about 5 MPa, at least about 10 MPa or even 20 Mpa or more, e.g., from about 0.5 to about 10 MPa, as determined by the tensile strength assay appearing in the Experimental Section, below.

In certain embodiments, the resultant product is stable in vivo for extended periods of time, by which is meant that it does not dissolve or degrade (exclusive of the remodeling activity of osteoclasts) under in vivo conditions, e.g., when implanted into a living being, for extended periods of time. In these embodiments, the resultant product may be stable for at least about 4 months, at least about 6 months, at least about 1 year or longer, e.g., 2.5 years, 5 years, etc. In certain embodiments, the resultant product is stable in vitro when placed in an aqueous environment for extended periods of time, by which is meant that it does not dissolve or degrade in an aqueous environment, e.g., when immersed in water, for extended periods of time. In these embodiments, the resultant product may be stable for at least 2 weeks, e.g., at least about 1 month, including at least about 4 months, at least about 6 months, at least about 1 year or longer, e.g., 2.5 years, 5 years, etc. The length of the time that the implant persists is determined by the extent to which it replaced by new bone via cell-mediated remodeling, which is primarily a stress-mediated process and thus dependent on the specific anatomical site.

In many embodiments, the settable paste-like composition is capable of setting in a fluid environment, such as an in vivo environment at a bone repair site. As such, the settable paste composition can set in a wet environment, e.g., one that is filled with blood and other physiological fluids. Therefore, the site to which the flowable composition is administered during use need not be maintained in a dry state.

Following preparation of the settable cement composition, as described above, it is introduced into a target bone site, e.g., with vibration, according to the present invention.

In certain embodiments, the settable cement composition is prepared at a location apart from the delivery element, e.g., syringe and needle. For example, the cement may be prepared in a mortar and pestle and then introduced into the delivery element for placement at the target site. Alternatively, the cement may be prepared in pouch or analogous structure, e.g., in its initial packaging (as described in U.S. Pat. No. 6,375,935; the disclosure of which is herein incorporated by reference). In yet other embodiments, the cement is prepared in the delivery element, e.g., syringe, as it is being vibrated according to the present invention, where the vibration of the delivery element provides the requisite agitation to combine the liquid and solid components of the cement. As such, the liquid and solid components are introduced separately into the delivery element, and vibration of the delivery element not only provides for delivery of the cement to the target site in a manner according to the invention (and described above) but also agitates or mixes the liquid and solid components to produce the flowable composition. In these latter embodiments, one may employ a delivery element that is preloaded with the liquid and solid components, where the components are separated by a frangible barrier that, upon agitation or other convenient trigger, is broken to allow mixing of the solid and liquid components, as desired.

Utility

The subject methods as described above find use in applications where it is desired to use an orthopedic cement that is a material capable of setting up into a solid product when placed at a physiological site of interest, such as in dental, craniomaxillofacial and orthopedic applications, as well as other application in which a bone defect filling composition is employed. In orthopedic applications, the cement will generally be prepared and introduced to a bone repair site, such as a bone site comprising cancellous bone. The subject methods find particular use in those applications where it is desired to introduce a cement into a cancellous bone target site in a manner such that the cement penetrates the cancellous bone to produce a cancellous bone/cement composite structure.

Representative orthopedic applications in which the invention finds particular use include the treatment of fractures and/or implant augmentation, in mammalian hosts, particularly humans. In such fracture treatment applications, the fracture is first reduced. Following fracture reduction, a settable structural material is introduced into the cancellous tissue in the fracture region using the delivery methods described above. Specific dental, craniomaxillofacial and orthopedic indications in which the subject invention finds use include, but are not limited to, those described in U.S. Pat. No. 6,149,655, the disclosure of which is herein incorporated by reference.

One particular representative application in which the subject compositions find use is vertebroplasty, particularly percutaneous vertebroplasty. Percutaneous vertebroplasty is a well-known procedure involving the injection of a bone cement or suitable biomaterial into a vertebral body via percutaneous route under imaging guidance, such as X-ray guidance, typically lateral projection fluoroscopy. The cement is injected as a semi-liquid substance through a needle that has been passed into the vertebral body, generally along a transpedicular or posterolateral approach. The four main indications are benign osteoporotic fractures, malignant metastatic disease, benign tumors of the bone, and prophylactic stabilization of vertebral body. Percutaneous vertebroplasty is intended to provide structural reinforcement of a vertebral body through injection, by a minimally invasive percutaneous approach, of bone cement into the vertebral body. See, for example, Cotton A., et al "Percutaneous vertebroplasty: State of the Art." Radiograhics 1998 March-April; 18(2):311-20; discussion at 320-3.

The general steps for performing a vertebroplasty are as follows. The patient is placed in the prone position and the skin overlying the fractured vertebrae is prepped and draped. A suitable local anesthetic such as 1% Lidocaine is injected into the skin underlying fat and into the periosteum of the pedicle to be entered. Next, a skin incision of about five millimeters is made with a No. 11 scalpel blade or other suitable surgical implement. The decision regarding which pedicle to use is made based on CT (computed tomography) and MR (magnetic resonance) images. A needle of an appropriate gauge (such as eleven gauge or thirteen gauge in a smaller vertebral body) is passed down the pedicle until it enters the vertebral body and reaches the junction of the anterior and middle thirds. This area is the region of maximum mechanical moment and usually the area of greatest compression. At this point a vertebrogram can be performed, if desired, by the injection of non-ionic X-ray contrast into the vertebral body to look for epidural draining veins.

Next, a cement is prepared, e.g., according to the methods as described above. The cement is then injected with vibration as described above under lateral X-Ray projection fluoroscopy imaging or other suitable imaging. The posterior aspect of the vertebral body is an important area to observe for posterior extension of cement, and it is generally accepted that this should be watched constantly during the injection. The injection is stopped as the cement starts to extend into some unwanted location such as the disc space or towards the posterior quarter of the vertebral body, where the risk of epidural venous filling and hence spinal cord compression is greatest. The injection is also discontinued if adequate vertebral filling is achieved. On average, about four to five cubic-centimeters of cement can be injected on each side, and it is known to inject up to about eight to ten cubic-centimeters per side.

Systems

Also provided are systems that find use in practicing the methods of the subject invention, as described above. Typically, the subject systems at least include: a cement handling element, e.g., mixing element, delivery element, shaping element, etc.; and a vibratory element for applying a vibratory force to the cement at some point during its preparation and/or use, as described above.

In a representative embodiment, the systems at least include: (a) a delivery device for the cement; and (b) a vibratory element for vibrating the flowable cement composition during delivery. The delivery device in many of these representative embodiments includes a flowable composition introduction element, such as a syringe and needle, where this element is typically attached to a reservoir of the cement composition, e.g., a syringe body filled with the cement.

The vibratory element may be any convenient means for vibrating the cement composition as it is introduced by the delivery device to the target bone site. A representative type of vibratory element that may be included in the subject systems is a device that vibrates a needle or analogous structure of a cement delivery device.

A representative device that is capable of vibrating a needle to deliver a cement to a target site according to the present invention is depicted in various views in FIGS. 1 to 6. As can be seen in FIG. 1, this representative vibratory element 10 is made up of a pneumatically driven vibrating disc 12 that includes a needle holder 14. When a needle of a cement delivery device (not shown) is present in the needle holder, vibration in the disc is transferred to the needle which, in turn, is transferred to the cement composition being delivered thereby. Also shown is handle 16 (which also serves as an air intake conduit) and exhaust piece 18, through which air leaves the device. The vibratory element is dimensioned for easy use with a calcium phosphate cement delivery element, and therefore typically ranges in length X from about 0.25 to 2.5 ft, such as from about 0.5 to about 1.5 feet, including from about 0.75 to about 1 feet; and a height Y ranging from about 0.5 to 12 in, such as from about 1 to about 10 inches, including from about 1 to about 5 inches.

Figure 2:
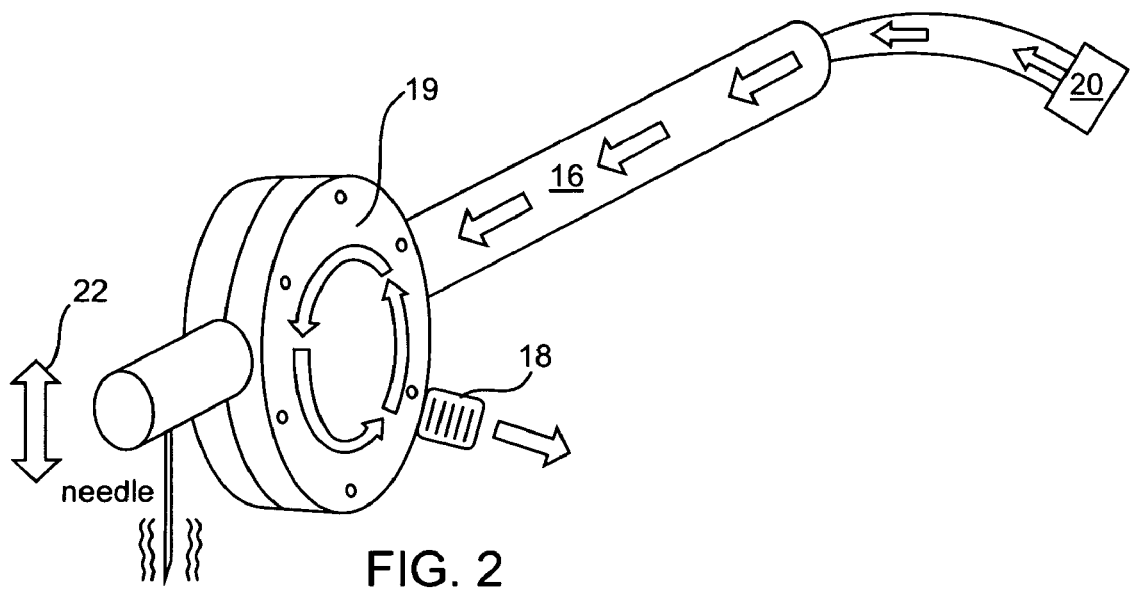

FIG. 2 provides another view of the device shown in FIG. 1, where the air flow through the device is depicted. In the device shown in FIG. 2, airflow generated by an air compressor 20 flows through the handle 16 and into an air intake port of a race or track 19 present inside of the disc. Air flows around the race and out the exhaust 18. Force produced by the air flow propels a steel bearing or ball (not shown) around the track at a high frequency. Momentum of the ball creates up and down vibration in the direction of arrow 22 that is transferred to a needle-holder and ultimately the material being dispensed by the needle. Vibration facilitates the flow of cement by reducing particle adhesion and literally "pushing" the cement downward.

Figure 3:
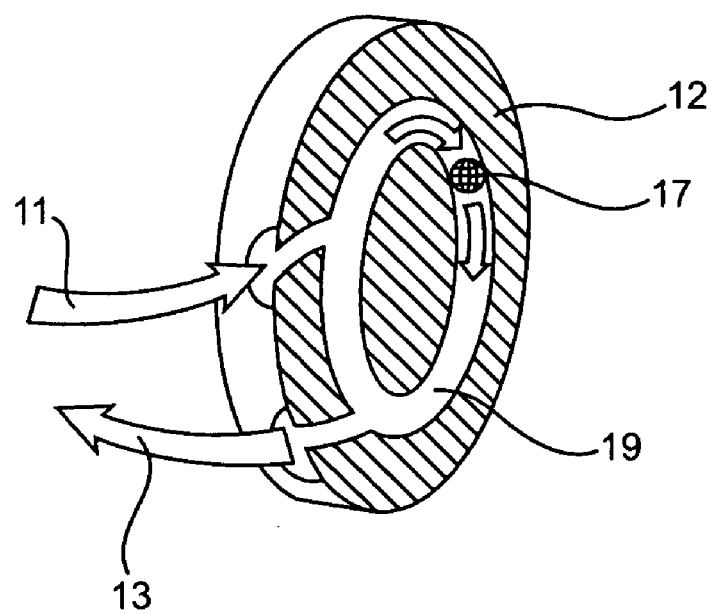

FIG. 3 provides another view of the disc 12 of the device. Shown in the depiction of FIG. 3, disc 12 includes race or track 19 around which ball 17 moves, as driven by air flowing from the intake 11 to the exhaust 13.

Figure 4:
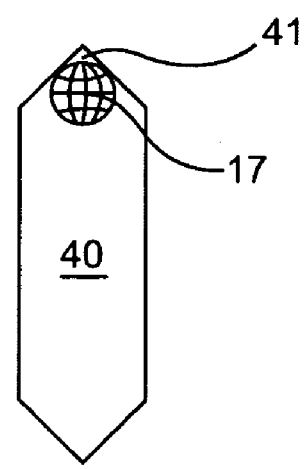

FIG. 4 provides a cross-sectional view of a representative race 40 and a ball 17 inside of the race. The race 40 has an angled end 41 along which the ball travels as it moves along the race.

Figure 5A:
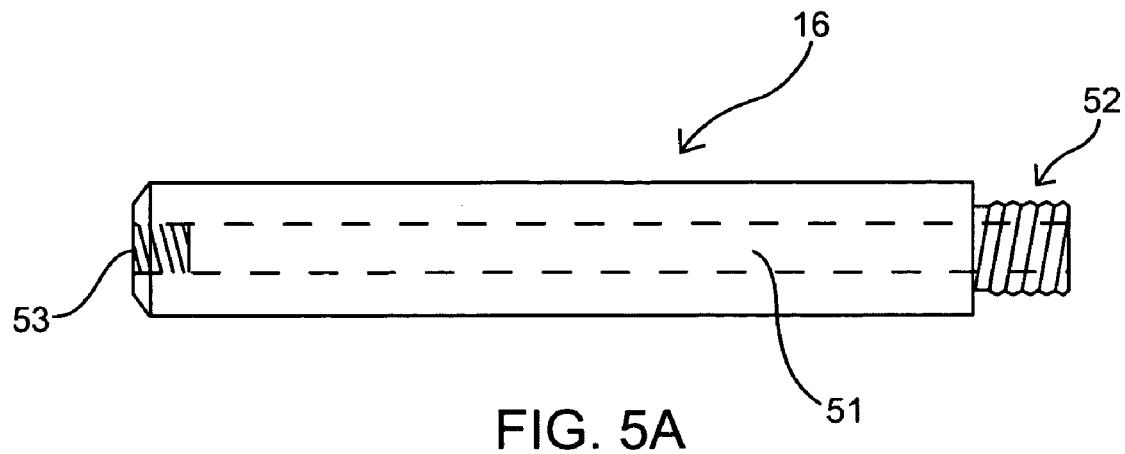
Figure 5B:
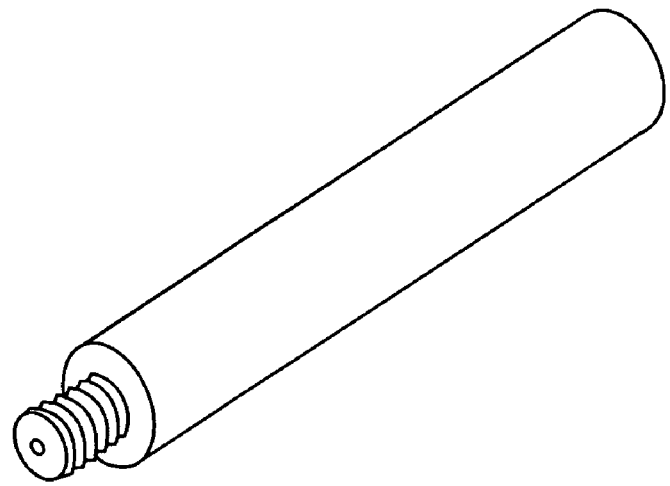

FIGS. 5A and 5B provide detailed views of the handle element 16. As shown in FIG. 5A, handle 16 includes an internal air flow passageway 51 for airflow from an external compressor to the race of the disc component 12. At one of the handle 16 is threaded disc attachment element 52, while at the other end is threaded receiving element 53 for attachment to an external air source, e.g., compressor. FIG. 5B provides an angled view of the handle shown in FIG. 5A.

FIGS. 6A to 6D provide various views of needle holder 14. FIG. 6A provides a side view of needle holder 14 showing a through-all hole 61 which is cut and countersunk to fit a delivery needle (not shown). Also shown is threaded disc attachment element 62, and through-all hole 63 for set screw. FIG. 6B provides a front view of the needle 14 showing the through-all hole 63 for the set screw 64, where hole 63 intersects hole 61. FIG. 6C shows a delivery element 65 positioned in hole 61 and held in place by set screw 64 positioned in hole 63. FIG. 6D provides an angled view of needle holder 14 holding a delivery needle 65.

In certain embodiments of the subject systems, the cement delivery device and the vibratory element are distinct from each other, i.e., they are separate devices. In yet other embodiments, the delivery device and vibratory element are found on a single integrated device or instrument.

As reviewed above, vibration may be employed in certain embodiments following delivery of the cement to a particular target site. A variety of different types of devices may be employed to apply vibration to a cement composition post delivery. Representative devices are shown in FIGS. 7A and 7B. The devices shown in FIGS. 7A and 7B, i.e., 71 and 72 respectfully, are identical in shape but different in size, and may be provided separately or together (e.g., in the form of a kit) so as to provide the user with greater flexibility depending on the particular application being performed. Devices 71 and 72 are "elevator" type devices that include an elongated central portion 73 and terminal flattened portions 74 and 75, which portions may have a "spatula" or analogous configuration. During use, an end of the elevtator devices is contacted with the delivered cement and the device is vibrated, thereby applying vibration to the cement.

In certain embodiments, the subject systems further include a cement composition or components thereof, as described above, where the components may or may not be combined into a flowable composition.

Devices

Also provided are icement delivery devices that include a vibratory element which is capable of vibrating a cement composition while it is being delivered, as described above. The vibrating element may be integral or separate from the other components of the device. For example, devices that include a vibrating cement delivery needle, where the vibration of the needle is provided by an element integral to the delivery device, are provided by the subject invention.

Kits

Also provided are kits for use in practicing the subject methods. The kits at least include one or more vibratory elements, as described above, for applying vibration to the cement at some point during it preparation and/or use, e.g., to a component of a delivery device so that a cement delivered by the delivery device can be delivered in accordance with the subject methods. In many embodiments, the kits also include a delivery device for delivering a cement composition, where in certain embodiments the delivery device and vibratory element may integrated into a single instrument, such that they are components of the same device.

In certain embodiments, the kits further include a calcium phosphate cement, where the dry and liquid components may be present in separate containers in the kit, or some of the components may be combined into one container, such as a kit wherein the dry components are present in a first portion and the liquid components are present in a second portion, where the portions are contained so they may or may not be present in a combined configuration, as described in U.S. Pat. No. 6,149,655, the disclosure of which is herein incorporated by reference. In certain embodiments, the kits may include two or more setting fluids in different concentrations, e.g., where one wishes to provide a kit with flexibility with respect to the nature of the setting fluid that is prepared therefrom. For example, a kit may include two or more different phosphate-silicate solutions that differ from each other with respect to their silicate and/or phosphate components. Alternatively, the kit may include to or more different, separate phosphate and/or silicate solutions that differ from each other in terms of concentration and that are mixed upon use of the kit as desired to obtain a desired setting fluid. As mentioned above, the kit components may be present in separate containers. Alternatively, the components may be present as a packaged element, such as those described above.

In addition to above-mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The following examples are offered by way of illustration and not by way of limitation.

Experimental

A. Cement Formulation

| 1. Liquid: Sodium Silicate 0.25 wt % | 2. Powder: | Moles |
|---|---|---|
| | CaHPO4 | 0.7 |
| | Ca$_3$(PO$_4$)$_2$ | 1.0 |
| | Ca(H$_2$PO$_4$)$_2$.H$_2$O | 0.15 |

The above liquid and powder components were combined in mortar and pestle mixing for one minute with a liquid to solid ratio of 0.40.

B. Representative Use 4 osteoporotic cadaveric vetebra were injected with the cement described in A above with or without the use of vibratory delivery using a pneumatic vibrator as depicted in FIGS. 1 to 6. Each delivery was done under fluroscopic imaging and the flow and amount of cement delivered qualitatively assessed. It was noted that significantly greater amounts of cement were delivered and a large reduction in pressure needed for injection was obtained with the use of vibration during delivery of the cement.

It is evident from the above results and discussion that improved methods (and devices for practicing the same) of using orthopedic cements are provided. Benefits of the subject methods include, but are not limited to: (a) improved cement preparation; (b) improved cement delivery, e.g., delivery which achieves highly controlled penetration of cancellous tissue without the use of high pressure; (c) efficient target site preparation; (d) ability to shape or configure a cement once positioned at a target site; etc. As such, the subject invention represents a significant contribution to the art.

All publications and patent applications mentioned in this specification are herein incorporated by reference to the same extent as if each individual publication or patent application was specifically and individually indicated to be incorporated by reference.

The invention now being fully described, it will be apparent to one of skill in the art that many changes and modifications can be made thereto without departing from the spirit and scope of the appended claims.

What is claimed is:

1. A method of introducing a calcium phosphate cement composition into a target bone site, said method comprising:
   engaging a needle holder with a threaded recess in a vibratory element;
   seating a needle in the needle holder;
   positioning a hardware device at a target bone site; and
   delivering said calcium phosphate cement composition to a target bone site through the needle to produce a composite fixation structure of said hardware device and said cement at said target site, wherein said cement is vibrated as it is delivered to said target bone site in a manner such that penetration of said cement into said target bone site stops substantially simultaneously with cessation of vibration.

2. The method according to claim 1, wherein a vibratory force is applied to said hardware device during said delivering.

3. The method according to claim 1, wherein said target bone site is part of a reduced fracture.

4. The method according to claim 1, wherein said target bone site comprises cancellous bone.

5. The method according to claim 1, wherein said cement is vibrated at a frequency ranging from about 0.1 to about 100,000 Hz.

6. The method according to claim 1, wherein said cement is vibrated in a manner that provides for controlled penetration of said cement into said target bone without use of substantial pressure.

7. The method according to claim 1, wherein said hardware device is a plate.

8. The method according to claim 1, wherein said hardware device is wire.

9. The method according to claim 1, wherein said hardware device is a screw.

10. The method according to claim 9, wherein said screw is a cannulated screw.

11. The method according to claim 1, wherein said cement composition is prepared in conjunction with vibration.

* * * * *